(12) United States Patent
Koch

(10) Patent No.: US 10,888,693 B2
(45) Date of Patent: Jan. 12, 2021

(54) DRUG PELLET INJECTOR NEEDLE AND METHOD

(71) Applicant: WARSAW ORTHOPEDIC, INC., Warsaw, IN (US)

(72) Inventor: Brian D. Koch, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 391 days.

(21) Appl. No.: 15/683,507

(22) Filed: Aug. 22, 2017

(65) Prior Publication Data

US 2019/0060625 A1     Feb. 28, 2019

(51) Int. Cl.
| | | |
|---|---|---|
| *A61M 31/00* | (2006.01) | |
| *A61M 5/32* | (2006.01) | |
| *A61M 5/315* | (2006.01) | |
| *A61B 17/34* | (2006.01) | |
| *G09B 23/28* | (2006.01) | |
| *A61M 37/00* | (2006.01) | |
| *A61M 25/00* | (2006.01) | |
| *A61B 90/00* | (2016.01) | |

(52) U.S. Cl.
CPC ....... *A61M 31/007* (2013.01); *A61B 17/3401* (2013.01); *A61B 17/3468* (2013.01); *A61M 5/31515* (2013.01); *A61M 5/31586* (2013.01); *A61M 5/3286* (2013.01); *A61M 5/3293* (2013.01); *A61M 37/0069* (2013.01); *G09B 23/285* (2013.01); *A61B 2090/3966* (2016.02); *A61M 25/007* (2013.01)

(58) Field of Classification Search
CPC ............ A61B 17/3401; A61B 17/3468; A61B 2090/3966; A61M 25/007; A61M 31/007; A61M 37/0069; A61M 5/31515; A61M 5/31586; A61M 5/3286; A61M 5/3293; G09B 23/285
See application file for complete search history.

(56) References Cited

U.S. PATENT DOCUMENTS

| | | | |
|---|---|---|---|
| 2,513,014 A | * | 6/1950 | Fields ............... A61M 37/0069 604/60 |
| 2,850,013 A | | 9/1958 | Cordis |
| 2,922,420 A | * | 1/1960 | Cheng ................ A61B 17/3401 604/272 |
| 4,377,380 A | * | 3/1983 | Vadas ...................... A61C 5/62 222/391 |
| 4,673,387 A | | 6/1987 | Phillips et al. |

(Continued)

FOREIGN PATENT DOCUMENTS

WO      20012031 A1    4/2001

OTHER PUBLICATIONS

European Search Report, European Patent Office, EP 18183623.0-1122, dated Jan. 31, 2019.

*Primary Examiner* — William R Carpenter
(74) *Attorney, Agent, or Firm* — Sorell, Lenna & Schmidt, LLP

(57) ABSTRACT

An injection includes a tube having opposite first and second ends. A hub is coupled to the first end. A sheath is coupled to the tube and the hub. The hub is movable relative to the tube to move the sheath between a first orientation in which the sheath covers an orifice in the second end and a second orientation in which the sheath is spaced apart from the orifice. Kits and methods of use are disclosed.

19 Claims, 2 Drawing Sheets

(56) References Cited

U.S. PATENT DOCUMENTS

| | | | |
|---|---|---|---|
| 4,790,312 A * | 12/1988 | Capuano, Sr. | ............................... A61B 17/320016 606/171 |
| 4,846,811 A | 7/1989 | Vanderhoof | |
| 4,926,877 A * | 5/1990 | Bookwalter | ....... A61B 10/0266 600/567 |
| 5,281,197 A * | 1/1994 | Arias | ................ A61M 37/0069 604/209 |
| 5,284,479 A | 2/1994 | De Jong | |
| 5,358,474 A * | 10/1994 | Kaldany | ............ A61B 10/0275 600/567 |
| 5,542,920 A | 8/1996 | Cherif Cheikh | |
| 5,695,463 A | 12/1997 | Cherif-Cheikh | |
| 5,997,513 A | 12/1999 | Smith et al. | |
| 7,794,432 B2 | 9/2010 | Young et al. | |
| 7,918,821 B2 | 4/2011 | Mahurkar | |
| 7,988,676 B1 | 8/2011 | Gray | |
| 8,048,035 B2 | 11/2011 | Mesa et al. | |
| 8,657,840 B2 * | 2/2014 | Palmer | ............. A61B 17/32002 606/170 |
| 9,289,563 B2 | 3/2016 | Pickhard et al. | |
| 10,413,313 B2 * | 9/2019 | Brown | ................ A61B 17/3472 |
| 2005/0038355 A1 * | 2/2005 | Gellman | ............ A61B 10/0275 600/564 |
| 2009/0148500 A1 | 6/2009 | Lawter et al. | |
| 2009/0270672 A1 | 10/2009 | Fago | |
| 2012/0209247 A1 | 8/2012 | Feng | |
| 2014/0081210 A1 * | 3/2014 | Bierman | ........... A61M 25/0606 604/164.03 |
| 2016/0376820 A1 | 12/2016 | Glover | |
| 2017/0119974 A1 * | 5/2017 | Racz | .................. A61B 17/3401 |
| 2017/0281251 A1 | 10/2017 | Davis et al. | |

* cited by examiner

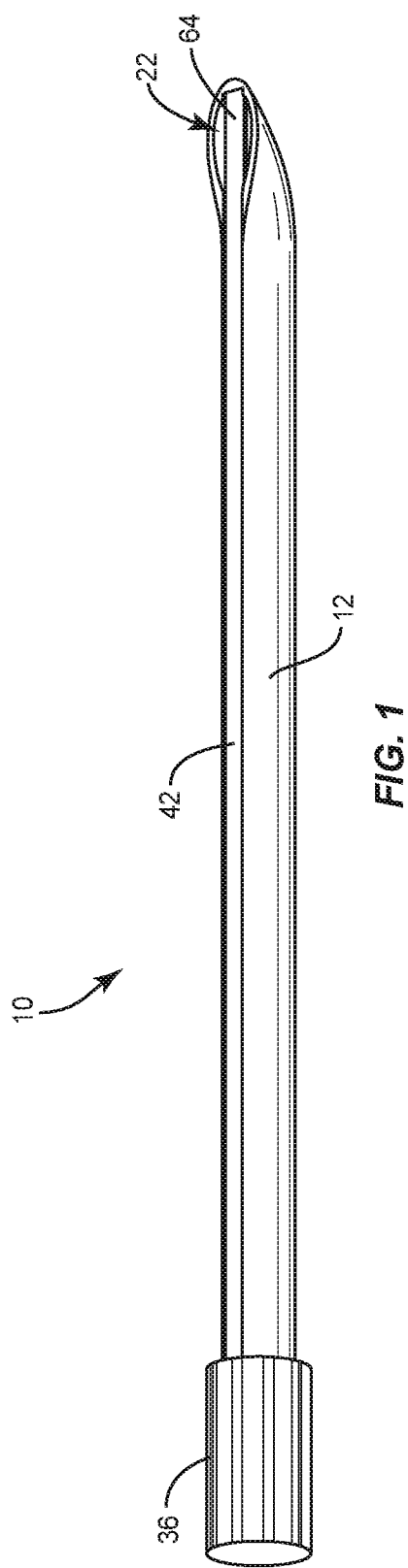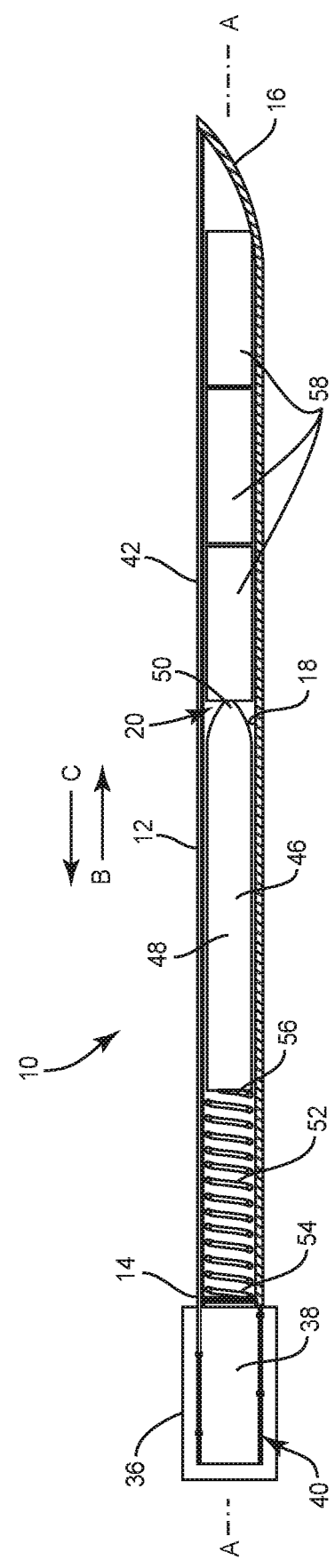

DRUG PELLET INJECTOR NEEDLE AND METHOD

TECHNICAL FIELD

The present disclosure generally relates to drug delivery devices, and more particularly to drug pellet injectors that are each configured to deploy one or more drug pellets.

BACKGROUND

Drugs may be delivered to patients by a variety of methods including oral, intravenous, intramuscular, inhalation, topical or subcutaneous delivery. The drug may be delivered directly or locally to the treatment site (e.g., intrathecally, intraspinally, intraarticularly, etc.). The method of delivery chosen depends upon, among other things, the condition being treated, and the desired therapeutic concentration of the drug to be achieved in the patient and the duration of drug concentration that must be maintained.

Drug depots, such as, for example, drug pellets have been developed, which allow a drug to be introduced or administered to sites beneath the skin of a patient. The drug pellets release the drug over a period of time. Drug pellets allow the drug to be released from the pellet in a relatively uniform dose over weeks, months or even years. Administering drugs using drug pellets is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Drug delivery devices have been developed to implant drug pellets within a patient. However, conventional devices are often cumbersome, may be difficult to operate, may not prevent the drug pellets from being misdirected as they move through the device and/or include numerous components. This increases the total time needed to perform a procedure and increases the likelihood of user error. This disclosure describes improvements over these prior art technologies.

SUMMARY

In one embodiment, an injection needle is provided. The injection needle includes a tube having opposite first and second ends. A hub is coupled to the first end. A sheath is coupled to the tube and the hub. The hub is movable relative to the tube to move the sheath between a first orientation in which the sheath covers an orifice in the second end and a second orientation in which the sheath is spaced apart from the orifice. In some embodiments, kits and methods of use are disclosed.

BRIEF DESCRIPTION OF THE DRAWINGS

The present disclosure will become more readily apparent from the specific description accompanied by the following drawings, in which:

FIG. 1 is a perspective view of one embodiment of a drug pellet delivery system in accordance with the present principles of the present disclosure;

FIG. 2 is a side view of the drug pellet delivery system shown in FIG. 1;

Like reference numerals indicate similar parts throughout the figures.

DETAILED DESCRIPTION

Figure 3:
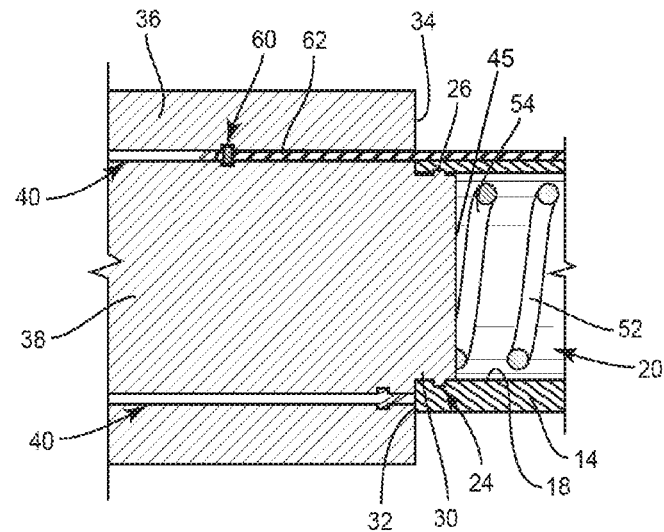
FIG. 3 is a side, cross sectional view of components of the drug pellet delivery system shown in FIG. 1.

The exemplary embodiments of a drug pellet delivery system and related methods are discussed in terms of medical devices for delivering drug pellets, such as, for example, one or a plurality of drug depots. In some embodiments, the system and method may be employed in applications that require at least one drug pellet to be implanted within a patient's body. In some embodiments, the system and method may be employed in applications to deliver one or more drug pellets into the epidural space of the lumbrosacral spine of a patient.

In some embodiments, the drug pellet delivery system includes a Tuohy epidural needle containing a spring, a plunger, drug pellets, and a sheath covering an exit orifice of the needle. The needle contains a mechanism to displace the sheath and activate the spring/plunger system to deploy the pellets. In some embodiments, the mechanism includes twisting the needle hub.

In some embodiments, the drug pellet delivery system includes a pellet injector needle having a small cannula that is about the size and shape of a standard Tuohy epidural needle. In some embodiments, the pellet injector needle is the only component needed to perform a procedure to inject drug pellets in a target location. In some embodiments, the pellet injector needle includes a spring-loaded plunger inside a probe to reduce the risk of user error and simplify the process of pellet deployment.

In some embodiments, the drug pellet delivery system includes a pellet injector needle that is an all-in-one concept to reduce the number of components of the system the user interacts with to one, and greatly simplify the deployment process. This will reduce the total time to perform the procedure as well as reduce the number of user errors. Additionally, there is a significant reduction in the total volume of the product, reducing packaging size.

In some embodiments, the drug pellet delivery system includes a pellet injector needle having a sheath, such as, for example, a stopper that prevents drug pellets from falling out of the injector needle until the stopper is moved out of an opening of a cannula of the injector needle. In some embodiments, the pellet injector needle includes a spring that engages a plunger. The spring is configured to be compressed against the plunger. Once the stopper is moved, the system will automatically deploy the pellets. A hub, such as, for example, a cap is attached to the cannula such that the cap can rotate about the cannula's center axis. A pin connects the stopper to the cap. The cap includes a helical track that the pin slides in. As the cap is rotated clockwise, the pin slides along the track and moves the stopper axially toward the cap. In some embodiments, two rotations of the cap are required to trigger the pellet deployment system inside of the cannula.

In some embodiments, one or all of the components of the drug pellet delivery system may be disposable, peel-pack, pre-packed sterile devices. In some embodiments, the components of the drug pellet delivery system are configured for one time use and are disposed after they are used one time.

However, it is contemplated that one or all of the components of the drug pellet delivery system may be reusable. The drug pellet delivery system may be configured as a kit with multiple sized and configured components, including, for example, various drug pellets or depots. In some embodiments, the drug pellets or depots are pre-loaded into a delivery device. In some embodiments, one or more of the components of the drug pellet delivery system are configured to be sterilized.

In some embodiments, the disclosed drug pellet delivery system and methods may be alternatively employed in a surgical treatment with a patient in a prone or supine position, and/or employ various surgical approaches, including anterior, posterior, posterior mid-line, direct lateral, postero-lateral, antero-lateral approaches, etc. in any body region. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. Men such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drug pellets or drug depots to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a drug pellet delivery system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there are illustrated components of a drug pellet delivery system 10 in accordance with the principles of the present disclosure.

The components of drug pellet delivery system 10 can be fabricated from biologically acceptable materials suitable for medical applications, including metals, synthetic polymers, ceramics and bone material and/or their composites, depending on the particular application and/or preference of a medical practitioner. For example, the components of drug pellet delivery system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of drug pellet delivery system 10 may have material composites, including the above materials, to achieve various desired characteristics such as strength, rigidity, elasticity, compliance, biomechanical performance, durability and radiolucency or imaging preference. The components of drug pellet delivery system 10, individually or collectively, may also be fabricated from a heterogeneous material such as a combination of two or more of the above-described materials. The components of drug pellet delivery system 10 may be monolithically formed, integrally connected or include fastening elements and/or instruments, as described herein.

In some embodiments, drug pellet delivery system 10 is used to deliver one or a plurality of drug pellets or drug depots. In some embodiments, the drug pellet or drug depots may include an active agent, such as, for example, one or a plurality of drugs.

Drug pellet delivery system 10 includes a tube, such as, for example, a cannula 12 that extends along a longitudinal axis A between an end 14 and an opposite end 16. Cannula 12 includes a surface 18 that defines a passageway 20 and an orifice 22 that is in communication with passageway 20. Cannula 12 is curved at end 16 such that orifice 22 extends transverse to axis A. In some embodiments, orifice 22 extends perpendicular to axis A. In some embodiments, orifice 22 may be disposed at alternate orientations, relative to axis A, such as, for example, acute or obtuse, co-axial and/or may be offset or staggered. In some embodiments, passageway 20 may have various cross section configurations, such as, for example, circular, oval, oblong, triangular, rectangular, square, polygonal, irregular, uniform, non-uniform, variable, tubular and/or tapered. In some embodiments, passageway 20 has a uniform diameter along the entire length of cannula 12. In some embodiments, cannula 12 is made from a biocompatible material that provides rigidity to cannula 12, such as, for example, stainless steel. In some embodiments, cannula 12 is a Tuohy epidural needle.

Figure 4:
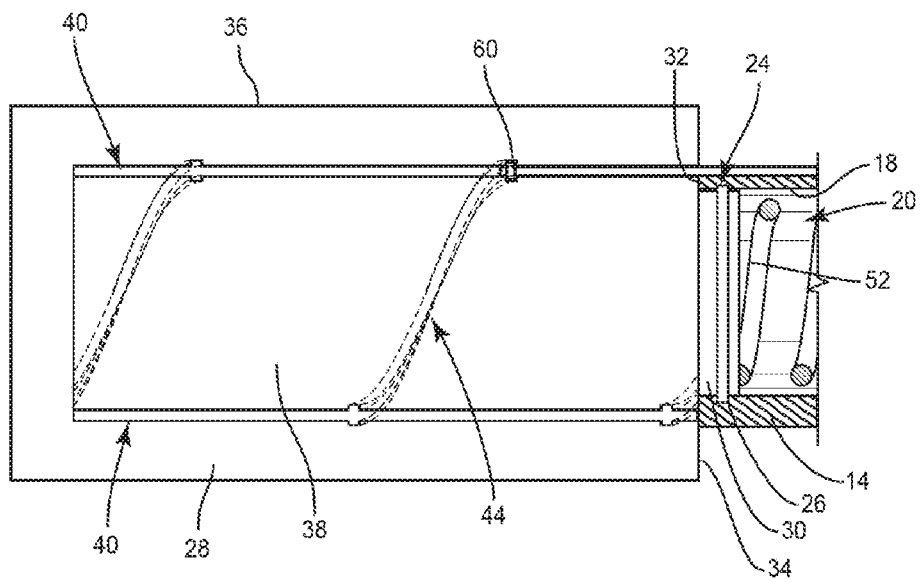
FIG. 4 is a side view, in part phantom, of components of the drug pellet delivery system shown in FIG. 1.

Cannula 12 includes a circumferential cavity 24 that extends into surface 18, as best shown in FIGS. 3 and 4. A flange 26 of a cap, such as, for example, a hub 28 is positioned within cavity 24 to couple hub 28 to cannula 12 such that hub 28 is rotatable relative to cannula 12 about axis A. As shown in FIGS. 3 and 4, an end 30 of hub 28 is positioned within passageway 20 to position flange 26 within cavity 24. In some embodiments, hub 28 can be variously connected with cannula 12, such as, for example, frictional engagement, threaded engagement, mutual grooves, screws, adhesive, nails, barbs and/or raised element.

Hub 28 includes a transverse surface 32 that directly engages an end surface 34 of cannula 12 when flange 26 is positioned within cavity 24. Hub 28 includes a handle having a gripping portion 36, an inner portion 38 and a circumferential channel 40 positioned between portion 36 and portion 38. Channel 40 is configured for disposal of a stopper, such as, for example, a sheath 42, as discussed herein. In some embodiments, an outer surface of portion 36 may have various surface configurations, such as, for example, smooth and/or surface configurations to enhance gripping, such as, for example, rough, arcuate, undulating, porous, semi-porous, dimpled, polished and/or textured, according to the requirements of a particular application. Portion 38 includes a helical track 44 that extends into an outer surface of portion 38, as shown in FIG. 4. Track 44 is configured to move sheath 42 between a first orientation in which sheath 42 covers at least a portion of orifice 22 and a second orientation in which sheath 44 is spaced apart from orifice 22, as discussed herein. As shown in FIG. 3, for example, portion 38 includes a wall 45 that extends perpendicular to axis A. Hub 28 is coupled to cannula 12 such that wall 45 extends across passageway 20 to block passageway 20.

System 10 includes a plunger 46 movably positioned within passageway 20, as shown in FIG. 2. Plunger 46 includes a body 48 having a cylindrical configuration and a tapered tip 50. A biasing member, such as, for example, a spring 52 is disposed within passageway 20. Spring 52 includes an end 54 that directly engages hub 28 and an end 56 that directly engages plunger 44. One or a plurality of drug depots, such as, for example, drug pellets 58 may be positioned within passageway 20 such that tip 50 of plunger 46 directly engages one of pellets 58, as shown in FIG. 2. Hub 28 rotates relative to cannula 12 to move spring 52 between a compressed configuration in which pellets 58 are maintained within passageway 20 and an uncompressed configuration. As spring 52 moves from the compressed configuration to the uncompressed configuration, spring 52 moves plunger 46 in the direction shown by arrow B in FIG. 2 to push one or more of pellets 58 through orifice 22 of cannula 12, as discussed herein.

A pin 60 is permanently fixed to an end 62 of sheath 42 to couple sheath 42 to hub 28. Pin 60 is positioned within track 44 such that when hub 28 is rotated relative to cannula 12 about axis A, pin 60 moves along track 44 to move sheath 42 relative to hub 28 and cannula 12 between a first orientation in which an end 64 of sheath 42 covers at least a portion of orifice 22 of cannula 12, as shown in FIG. 1, and a second orientation in which end 64 of sheath 42 is spaced apart from orifice 22. As sheath 42 moves from the first orientation to the second orientation, sheath 42 moves along axis A in the direction shown by arrow C in FIG. 2. When sheath 42 is in the first orientation, sheath 42 blocks orifice 22 to prevent pellets 58 from exiting cannula 12 through orifice 22. When sheath 42 is in the second orientation, spring 52 moves from the compressed configuration to the uncompressed configuration to move plunger 46 in the direction shown by arrow B such that plunger 46 pushes at least one of pellets 58 through orifice 22.

In assembly, operation and use, system 10 is employed with a surgical procedure, such as, to deliver one or more drug pellets or drug depots, such as, for example drug pellets 58 to a target location within a patient. In some embodiments, the target location is the epidural space of the lumbrosacral spine.

For example, system 10 and accessories thereof, described above, can be employed to implant one or more drug pellets within a patient at a selected location, such as, for example, a surgical site. In use, a medical practitioner obtains access to the surgical site in any appropriate manner, such as, for example, via an incision. It is envisioned that system 10 can be used in any existing surgical method or technique including open surgery, mini-open surgery, minimally invasive surgery and percutaneous surgical implantation. One or more drug pellets can be delivered to the target location using system 10.

System 10 may be assembled by inserting one or more drug pellets or drug depots, such as, for example, drug pellets 58 within passageway 20 of cannula 12. In some embodiments, one or more pellets 58 are pre-loaded into cannula 12. That is, system 10 may be delivered to a medical practitioner with pellets 58 already positioned within cannula 12.

Cannula 12 is inserted through the incision to position cannula 12 within the patient such that orifice 22 of cannula 12 is positioned adjacent to the target location with sheath 42 in the first orientation to prevent pellets 58 from exiting cannula 12 through orifice 22. Hub 28 is then rotated relative to cannula 12 about axis A such that pin 60 moves along track 44 to move sheath 42 relative to hub 28 and cannula 12 along axis A in the direction shown by arrow C to move end 64 of sheath 42 such that end 64 is spaced apart from orifice 22. Moving sheath 42 from the first orientation to the second orientation causes spring 52 to move from the compressed configuration to the uncompressed configuration to move plunger 46 in the direction shown by arrow B such that plunger 46 pushes at least one of pellets 58 through orifice 22 to the target location.

In some embodiments, at least one of the components of system 10 can be made of radiolucent materials such as polymers. In some embodiments, cannula 12 is made from a radiopaque material. Radiomarkers may be included for identification under x-ray, fluoroscopy, CT or other imaging techniques.

It is envisioned that the use of image guided technologies may be employed with the aid of the system 10. Upon completion of the procedure, cannula 12 is removed from the patient and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An injection needle comprising:
    a tube extending in a straight line along a longitudinal axis between opposite first and second ends, the tube defining a passageway, the second end including an orifice that is in communication with the passageway, the orifice extending perpendicular to the axis such that no portion of the orifice is coaxial with the axis;
    a hub coupled to the first end, the hub comprising an outer portion, an inner portion and a circumferential channel positioned between the outer portion and the inner portion, the inner portion comprising a wall, the hub being coupled to the tube such that the wall extends across the passageway to block the passageway;
    a plunger positioned within the tube;
    a biasing member positioned between the hub and the plunger; and
    a sheath having a proximal end disposed in the channel, wherein the hub is movable relative to the tube to move the sheath between a first orientation in which a distal end of the sheath covers the orifice and a second orientation in which the sheath is spaced apart from the orifice.

2. An injection needle as recited in claim 1, wherein the hub is rotatable relative to the tube to move the sheath from the first orientation to the second orientation.

3. An injection needle as recited in claim 1, wherein the tube comprises an inner surface defining the passageway and a cavity that extends into the inner surface, the hub comprising a flange that is positioned within the cavity to allow the hub to rotate relative to the tube to move the sheath from the first orientation to the second orientation.

4. An injection needle as recited in claim 1, further comprising a pin positioned within the channel that couples the sheath to the hub.

5. An injection needle as recited in claim 1, further comprising a pin positioned within the channel that couples the sheath to the hub, the inner portion comprising a track, the pin being movable along the track as the hub is moved relative to the tube.

6. An injection needle as recited in claim 1, further comprising a pin positioned within the channel that couples the sheath to the hub, the inner portion comprising a helical track, the pin being movable along the helical track as the hub is rotated relative to the tube to move the sheath from the first orientation to the second orientation.

7. An injection needle as recited in claim 1, wherein the biasing member is a spring having a first end that engages the hub and a second end that engages the plunger.

8. An injection needle as recited in claim 1, wherein the tube is linear along the longitudinal axis along an entire length of the tube.

9. An injection needle as recited in claim 1, wherein the orifice extends transverse to the passageway.

10. An injection needle as recited in claim 1, wherein the tube comprises stainless steel.

11. An injection needle as recited in claim 1, wherein the tube is a Tuohy epidural needle.

12. An injection needle as recited in claim 1, wherein the tube comprises an inner surface defining the passageway, the first end defining an opening, the opening being in communication with the passageway, the hub being positioned within the opening such that the hub blocks the opening.

13. An injection needle as recited in claim 1, wherein the wall extends perpendicular to the longitudinal axis.

14. An injection needle as recited in claim 1, wherein the tube comprises opposite inner and outer surfaces, the inner surface defining the passageway, the sheath comprising an inner surface that directly engages the outer surface of the tube, the inner surface of the sheath sliding along the outer surface of the tube as the sheath moves between the first and second orientations.

15. An injection needle comprising:
    a cannula extending in a straight line along a longitudinal axis between opposite first and second ends, the cannula defining a passageway, the second end including an orifice that is in communication with the passageway, the orifice extending perpendicular to the axis such that no portion of the orifice is coaxial with the axis;
    a hub coupled to the first end, the hub comprising an outer portion, an inner portion and a circumferential channel positioned between the outer portion and the inner portion, the inner portion comprising a wall extending perpendicular to the longitudinal axis, the hub being coupled to the cannula such that the wall extends across the passageway to block the passageway;
    a plunger positioned within the cannula;
    a biasing member positioned between the hub and the plunger; and
    a sheath having a proximal end disposed in the channel, wherein the hub is rotatable relative to the cannula to move the sheath between a first orientation in which a distal end of the sheath covers the orifice and a second orientation in which the sheath is spaced apart from the orifice.

16. An injection needle as recited in claim 15, wherein the cannula comprises an inner surface defining the passageway and a cavity that extends into the inner surface, the hub comprising a flange that is positioned within the cavity to allow the hub to rotate relative to the cannula to move the sheath from the first orientation to the second orientation.

17. An injection needle as recited in claim 15, further comprising a pin positioned within the channel that couples the sheath to the hub, the inner portion comprising a track, the pin being movable along the track as the hub is moved relative to the cannula.

18. An injection needle as recited in claim 15, further comprising a pin positioned within the channel that couples the sheath to the hub, the inner portion comprising a helical track, the pin being movable along the helical track as the hub is rotated relative to the cannula to move the sheath from the first orientation to the second orientation.

19. An injection needle comprising:
    a stainless steel tube extending in a straight line along a longitudinal axis between opposite first and second ends, the tube including opposite inner and outer surfaces, the inner surface defining a passageway, the second end comprising an orifice that is in communication with the passageway, the orifice extending perpendicular to the longitudinal axis such that no portion of the orifice is coaxial with the longitudinal axis;

a hub coupled to the first end, the hub comprising an outer portion, an inner portion and a circumferential channel positioned between the outer portion and the inner portion, the inner portion comprising a wall extending perpendicular to the longitudinal axis, the hub being coupled to the tube such that the wall extends across the passageway to block the passageway;

a sheath having a proximal end disposed in the channel such that an inner surface of the sheath engages the outer surface of the tube; and a pin positioned within the channel that couples the sheath to the hub, the inner portion comprising a helical track, wherein the hub is rotatable relative to the tube to move the sheath such that the inner surface of the sheath slides long the outer surface of the tube between a first orientation in which the distal end of the sheath covers a portion of the orifice and a second orientation in which the sheath is spaced apart from the orifice, and wherein the pin is movable along the helical track as the hub is rotated relative to the tube to move the sheath from the first orientation to the second orientation.

* * * * *